United States Patent
Hosokawa et al.

(10) Patent No.: US 12,043,606 B2
(45) Date of Patent: *Jul. 23, 2024

(54) FLUOROLACTONE AND METHOD FOR PRODUCING SAME

(71) Applicant: DAIKIN INDUSTRIES, LTD., Osaka (JP)

(72) Inventors: Moe Hosokawa, Osaka (JP); Koutarou Hayashi, Osaka (JP); Yoshihiro Yamamoto, Osaka (JP); Akiyoshi Yamauchi, Osaka (JP); Makoto Matsuura, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 91 days.

This patent is subject to a terminal disclaimer.

(21) Appl. No.: 17/521,155

(22) Filed: Nov. 8, 2021

(65) Prior Publication Data
US 2022/0064139 A1 Mar. 3, 2022

Related U.S. Application Data

(63) Continuation of application No. PCT/JP2020/019137, filed on May 13, 2020.

(30) Foreign Application Priority Data

May 13, 2019 (JP) ................. 2019-090705

(51) Int. Cl.
*C07D 319/12* (2006.01)
(52) U.S. Cl.
CPC .................. *C07D 319/12* (2013.01)
(58) Field of Classification Search
CPC .................................................. C07D 319/12
See application file for complete search history.

(56) References Cited

U.S. PATENT DOCUMENTS

| 3,308,107 A | 3/1967 | Selman et al. |
| 3,450,716 A | 6/1969 | Selman |

(Continued)

FOREIGN PATENT DOCUMENTS

| CN | 108675983 | 10/2018 |
| EP | 3 925 954 | 12/2021 |

(Continued)

OTHER PUBLICATIONS

Kim "PubChem in 2021: new data content and improved web interfaces" Nucleic Acids Research, 2021, vol. 49, Database issue Published online Nov. 5, 2020.*

(Continued)

*Primary Examiner* — David K O'Dell
(74) *Attorney, Agent, or Firm* — WENDEROTH, LIND & PONACK, L.L.P.

(57) ABSTRACT

The present disclosure provides, for example, a method that can produce a fluorolactone compound from hexafluoropropylene oxide or the like in a single step. The present disclosure relates to a method for producing a compound represented by formula (1):

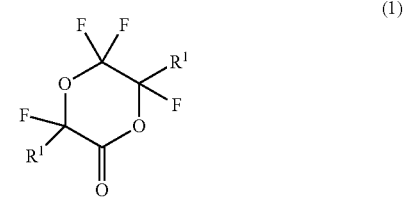

wherein two $R^1$ are the same and each is a fluorine atom or a fluoroalkyl group,
the method comprising step A of reacting a compound represented by formula (2):

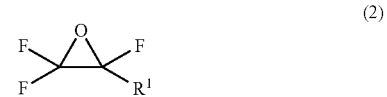

wherein $R^1$ is as defined above, with a compound represented by formula (3):

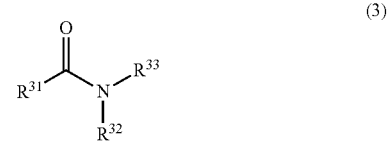

wherein $R^{31}$, $R^{32}$, and $R^{33}$ are the same or different and each is a hydrogen atom or an alkyl group, or two of them are optionally linked to each other to form a ring optionally having one or more substituents, and a compound represented by formula (4-1) or the like:

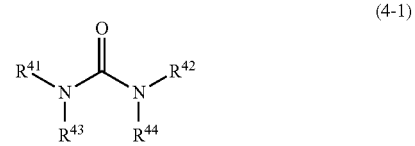

wherein $R^{41}$, $R^{42}$, $R^{43}$, and $R^{44}$ are the same or different and each is a hydrogen atom ox an alkyl group, or two of them are optionally linked to each other to form a ring optionally having one or more substituents.

12 Claims, No Drawings

(56) References Cited

U.S. PATENT DOCUMENTS

| | | | |
|---|---|---|---|
| 4,118,399 A | 10/1978 | Martini | |
| 2021/0371392 A1* | 12/2021 | Hosokawa | C07D 317/42 |

FOREIGN PATENT DOCUMENTS

| | | |
|---|---|---|
| JP | 52-142078 | 11/1977 |
| JP | 2005-2014 | 1/2005 |

OTHER PUBLICATIONS

Irwin "ZINC—A Free Database of Commercially Available Compounds for Virtual Screening" J. Chem. Inf. Model. 2005, 45, 177-182.*

"Find ETDs Home » Thesis Resources » Find ETDs" Online: "https://ndltd.org/thesis-resources/find-etds/" Accessed Jan. 31, 2023.*

Bartlett "Exploiting Chemical Diversity for Drug Discovery" Edited by Paul A Bartlett and Michael Entzeroth, The Royal Society of Chemistry, 2006, pp. 113-118.*

Registry/Zregistry (CAS REGISTRYSM) Sep. 2016 2 pages.*

Scifinder Results for HFPO suppliers Dec. 20, 2023.*

Experimental Organic Chemistry MacMillan: London, 1984, "Calculation of Yields" p. 220.*

"Hexafluoropropylene Oxide (HFPO) Product Information Sheet" 2018 The Chemours Company FC, LLC.*

Partial European Search Report dated Dec. 13, 2022 in corresponding European Patent Application No. 20806085.5.

International Search Report issued Aug. 4, 2020 in International (PCT) Application No. PCT/JP2020/019137.

Mikes et al., "Synthesis and Characterization of an Amorphous Perfluoropolymer: Poly(perfluoro-2-methylene-4-methyl-1,3-dioxolane)", Macromolecules, 2005, vol. 38, No. 10, pp. 4237-4245.

The Fifth Series of Experimental Chemistry 16, Synthesis of Organic Compounds IV, carboxylic acid, amino acid, peptide, vol. 16, 2007, p. 10, with partial English translation.

Yuminov et al., Perfluorinated Dioxolanes, Bulletin of the Academy of Sciences of the USSR, 1988, vol. 37, No. 2, Part 2, pp. 311-315.

Extended European Search Report issued Feb. 20, 2023 in corresponding European Patent Application No. 20806085.5.

Thomas Martini, "Die Umsetzung Von Hexamethylphosphorsaeuretriamid Mit Hexafluorpropenepoxid", Tetrahedron Letters, vol. 17, No. 22, pp. 1857-1860, 1976.

* cited by examiner

FLUOROLACTONE AND METHOD FOR PRODUCING SAME

TECHNICAL FIELD

The present disclosure relates to fluorolactone, a method for producing the same, and the like.

BACKGROUND ART 2-(Difluoromethylene)-4,4,5-trifluoro-5-(trifluoromethyl)-1,3-dioxolane is used as a fluororesin raw material. As a method for producing perfluorodioxolane, a method using 3,5,5,6-tetrafluoro-3,6-bis(trifluoromethyl)-1,4-dioxane-2-one as a raw material is known, as shown in the following formula (e.g., PTL 1).

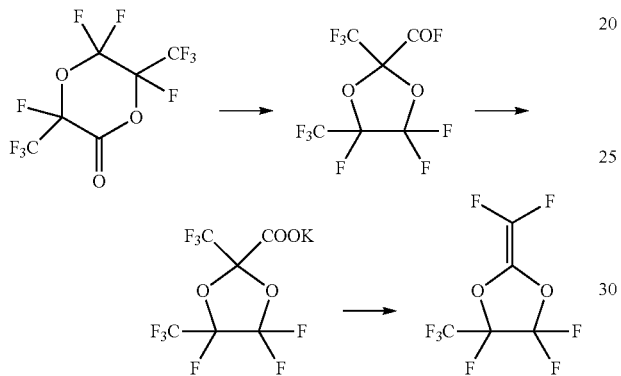

Further, as a method for producing perfluorodioxane, for example, a two-step method using hexafluoropropylene oxide as a raw material is known, as shown in the following formula (e.g., NPL 1),

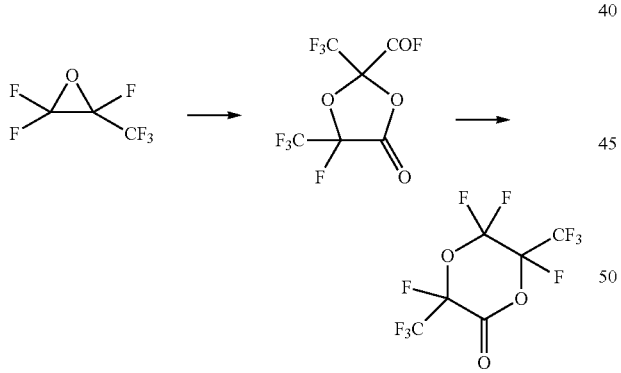

CITATION LIST

Patent Literature

PTL 1: JP2005-2014A

Non-Patent Literature

NPL 1: "Perfluorinated dioxolanes 1. Synthesis of some derivatives of perfluoro-4-oxo-1,3-dioxolane," V. S. Yumi- nov, S. V. Kartsov, V. L. Maksimov, and A. V. Fokin, Bulletin of the Academy of Sciences of the USSR, 1988, 37(2), 311-315.

SUMMARY

The present disclosure includes, for example, the following embodiment.

A method for producing a compound represented by formula (1):

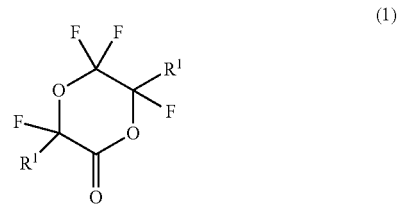

wherein two $R^1$ are the same and each is a fluorine atom or a fluoroalkyl group, the method comprising step A of reacting a compound represented by formula (2):

wherein $R^1$ is as defined above, with a compound represented by formula (3):

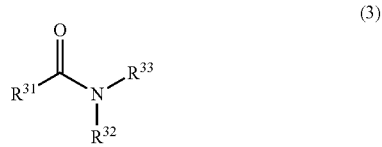

wherein $R^{31}$, $R^{32}$, and $R^{33}$ are the same or different and each is a hydrogen atom ox an alkyl group, or two of them are optionally linked to each other to form a ring optionally having one or more substituents; and at least one compound (4) selected from the group consisting of:

a compound represented by formula (4-1):

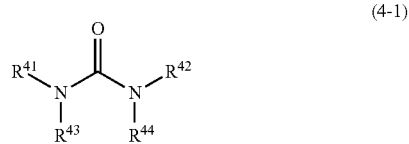

wherein $R^{41}$, $R^{42}$, $R^{43}$, and $R^{44}$ are the same or different and each is a hydrogen atom or an alkyl group, or two of them are optionally linked to each other to form a ring optionally having one or more substituents; and a compound represented by formula (4-2):

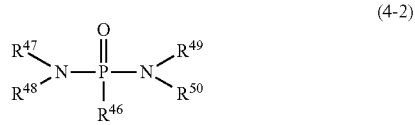

(4-2)

wherein $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{43}$ and $R^{50}$ are optionally linked to each other to form a ring optionally having one or more substituents, or $R^{49}$ and $R^{50}$ are optionally linked to each other to form a ring optionally having one or more substituents.

Advantageous Effects

The present disclosure provides, for example, a method that can produce a fluorolactone compound from hexafluoropropylene oxide or the like in a single step. The present disclosure provides a novel fluorodioxolane compound, a method for producing the same, and the like. According to the present disclosure, the yield of a fluorolactone compound in step A is high, whereby the purification of fluorolactone can be simplified, or the reaction liquid obtained in step A can be used as it is in other reactions (e.g., synthesis of a flucrodioxolane compound) using a fluorolactone compound as a raw material or an intermediate.

DESCRIPTION OF EMBODIMENTS

The above summary of the present disclosure is not intended to describe each disclosed embodiment or every implementation of the present disclosure.

The following description of the present disclosure illustrates embodiments of examples in more detail.

In several parts of the present disclosure, guidance is provided through examples, and these examples can be used in various combinations.

In each case, the group of examples can act as a non-exclusive and representative group.

All publications, patents, and patent applications referred to herein are incorporated herein by reference without modification.

Terms

Unless otherwise specified, the symbols and abbreviations in the present specification can be understood in the sense commonly used in the technical field to which the present disclosure pertains, according to the context of the present specification.

In the present specification, the terms "contain" and "comprise" are used with the intention to include the terms "consist essentially of" and "consist of."

Unless otherwise specified, the steps, treatments, or operations described in the present specification can be performed at room temperature.

In the present specification, room temperature can mean a temperature in the range of 10 to 40° C.

In the present specification, the notation "$C_{n-m}$" (where n and m are numbers) indicates that the number of carbon atoms is n or more and m or less, as is commonly understood by a person skilled in the art.

In the present specification, unless otherwise specified, examples of the "halogen atom" may include fluorine, chlorine, bromine, and iodine.

In the present specification, unless otherwise specified, examples of the "ring optionally having one or more substituents" in formula (3) may include a pyrrolidine ring, a piperidine ring, a pyrrolidone ring, and a piperidinone ring. Specific examples may include a 1-pyrrolidine ring, a 1-piperidine ring, a 2-pyrrolidone ring, and a 2-piperidone ring.

In the present specification, unless otherwise specified, examples of the "ring optionally having one or more substituents" in formula (4-1) may include a tetrahydropyrimidinone ring, an imidazolidinone ring, a pyrrolidine ring, and a piperidine ring. Specific examples may include a tetrahydropyrimidin-2-one ring, a 2-imidazolidinone ring, a 1-pyrrolidine ring, and a 1-piperidine ring.

In the present specification, unless otherwise specified, examples of the "ring optionally having one or more substituents" in formula (4-2) may include a diazaphospholidine oxide ring, a pyrrolidine ring, and a piperidine ring. Specific examples may include a diazaphospholidine-2-oxide ring, a 1-pyrrolidine ring, and a 1-piperidine ring.

In the present specification, unless otherwise specified, examples of the "substituent" include halogen atoms, alkyl groups, cyano groups, amino groups, alkoxy groups, and alkylthio groups. The number of substituents can be within the range from one to the maximum substitutable number (e.g., 1, 2, 3, 4, 5, or 6), preferably 1 to 4, more preferably 1 to 3, and particularly preferably 1 or 2. Two or more substituents may be the same or different.

In the present specification, unless otherwise specified, the "organic group" refers to a group formed by removing one hydrogen atom from an organic compound. As can be understood from this, organic groups have one or more carbon atoms.

In the present specification, unless otherwise specified, the "organic group" includes:
(1) a hydrocarbon group, and
(2) a hydrocarbon group having one or more heteroatoms (e.g., nitrogen, oxygen, sulfur, phosphorus, and halogen).

In the present specification, unless otherwise specified, the "hydrocarbon group" refers to a group consisting of carbon and hydrogen. Hydrocarbon groups are also called "hydrocarbyl groups."

In the present specification, unless otherwise specified, examples of the "hydrocarbon group" include:
(1) aliphatic hydrocarbon groups optionally substituted with one or more aromatic hydrocarbon groups (e.g., benzyl groups); and
(2) aromatic hydrocarbon groups optionally substituted with one or more aliphatic hydrocarbon groups.

Aromatic hydrocarbon groups are also called "aryl groups."

In the present specification, unless otherwise specified, the "aliphatic hydrocarbon group" can have a linear, branched, or cyclic structure, or a combination thereof.

In the present specification, unless otherwise specified, the "aliphatic hydrocarbon group" can be saturated or unsaturated.

In the present specification, unless otherwise specified, examples of the "aliphatic hydrocarbon group" include alkyl groups, alkenyl groups, alkynyl groups, and cycloalkyl groups.

In the present specification, unless otherwise specified, examples of the "alkyl group" include linear or branched $C_{1-10}$ alkyl groups, such as methyl, ethyl, propyl (e.g., n-propyl and isopropyl), butyl (e.g., n-butyl, isobutyl, sec-butyl, and tert-butyl), pentyl (e.g., n-pentyl, tert-pentyl, neopentyl, isopentyl, sec-pentyl, and 3-pentyl), hexyl, heptyl, octyl, nonyl, and decyl.

In the present specification, unless otherwise specified, examples of the "alkenyl group" include linear or branched $C_{1-10}$ alkenyl groups. Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, unless otherwise specified, examples of the "alkynyl group" include linear or branched $C_{2-6}$ alkynyl groups. Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, unless otherwise specified, examples of the "cycloalkyl group" include $C_{3-10}$ cycloalkyl groups. Specific examples include cyclopropyl, cyclobutyl, cyclopentyl, cyclohexyl, cycloheptyl, cyclooctyl, and adamantyl.

In the present specification, unless otherwise specified, examples of the "aromatic hydrocarbon group" (aryl group) include $C_{6-14}$ aromatic hydrocarbon groups ($C_{6-14}$ aryl groups). Specific examples include phenyl, naphthyl, phenanthryl, anthryl, and pyrenyl.

In the present specification, unless otherwise specified, examples of the "aromatic hydrocarbon ring" include $C_{6-16}$ aromatic hydrocarbon rings. Specific examples include benzene, naphthalene, anthracene, and phenanthrene rings.

In the present specification, unless otherwise specified, the "alkoxy group" may be a group represented by RO—, wherein R is an alkyl group (e.g., a $C_{1-11}$ alkyl group), such as a $C_{1-11}$ alkoxy group (e.g., methoxy, ethoxy, propoxy, isopropoxy, n-butoxy, isobutoxy, sec-butoxy, pentyloxy, or hexyloxy).

In the present specification, unless otherwise specified, the "fluoroalkyl group" refers to a group formed by replacing one or more hydrogen atoms of an alkyl group with a fluorine atom, and also includes a perfluoroalkyl group formed by replacing all the hydrogen atoms of an alkyl group. Examples of the "fluoroalkyl group" include linear or branched $C_{1-10}$ fluoroalkyl groups, such as mono-, di-, or trifluoromethyl, mono-, di-, tri-, tetra-, or hexafluoroethyl, mono-, di-, tri-, tetra-, hexa-, or heptafluorobutyl, mono-, di-, tri-, tetra-, hexa-, hepta-, octa-, or nonafluorobutyl, and mono-, di-, tri-, tetra-, hexa-, hepta-, octa-, nona-, deca-, or undecafluoropentyl.

In the present specification, unless otherwise specified, the "amino group optionally having one or more substituents" may be an amino group, a mono $C_{1-10}$ alkylamino group, or a di $C_{1-10}$ alkylamino group (two alkyl groups may be the same or different and are optionally linked to each other to form a ring). Specific examples include amino, methylamino, ethylamino, propylamino, isopropylamino, dimethylamino, diethylamino, dipropylamino, diisopropylamino, ethylmethylamino, methylpropylamino, methylisopropylamino, ethylpropylamino, pyrrolidyl, piperidyl, and ethylisopropylamino, unless otherwise specified.

Methods for Producing Compound Represented by Formula (1)

An embodiment of the present disclosure is a method for producing a compound represented by formula (1):

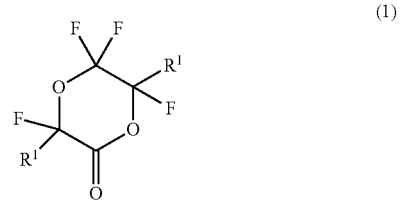

wherein two $R^1$ are the same and each is a fluorine atom or a fluoroalkyl group (in the present specification, also referred to as "compound (1)").

This method comprises step A of reacting a compound represented by formula (2):

wherein $R^1$ is as defined above (in the present specification, also referred to as "compound (2)"), with a compound represented by formula (3):

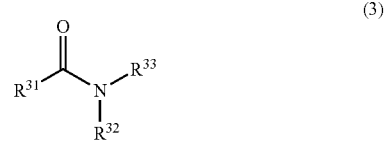

wherein $R^{31}$, $R^{32}$, and $R^{33}$ are the same or different and each is a hydrogen atom or an alkyl group, or two of them are optionally linked to each other to form a ring optionally having one or more substituents (in the present specification, also referred to as "compound (3)"); and at least one compound (4) selected from the group consisting of:

a compound represented by formula (4-1):

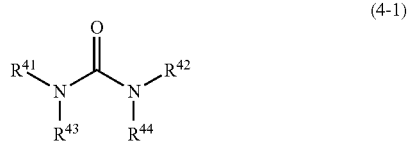

wherein $R^{41}$, $R^{42}$, $R^{43}$, and $R^{44}$ are the same or different and each is a hydrogen atom or an alkyl group, or two of them are optionally linked to each other to form a ring optionally having one or more substituents (in the present specification, also referred to as "compound (4-1)"); and a compound represented by formula (4-2):

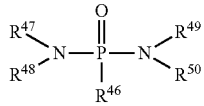

(4-2)

wherein $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{49}$ and $R^{50}$ are optionally linked to each other to form a ring optionally having one or more substituents, or $R^{49}$ and R are optionally linked to each other to form a ring optionally having one or more substituents (in the present specification, also referred to as "compound (4-2)").

$R^1$ is preferably a fluorine atom or a $C_{1-10}$ fluoroalkyl group, more preferably a fluorine atom or a $C_{1-5}$ perfluoroalkyl group, even more preferably a fluorine atom or a $C_{1-3}$ perfluoroalkyl group, and particularly preferably a $C_{1-3}$ perfluoroalkyl group.

Preferred specific examples of compound (2) include hexafluoropropylene oxide, 2,2,3-trifluoro-3-(perfluoroethyl)oxirane, and 2,2,3-trifluoro-3-(perfluoropropyl)oxirane.

Preferably, $R^{31}$, $R^{32}$, and $R^{33}$ are the same or different and each is a hydrogen atom or a $C_{1-5}$ alkyl group;

$R^{31}$ is a hydrogen atom or a $C_{1-5}$ alkyl group, $R^{32}$ and $R^{33}$ are linked to form a pyrrolidine ring or piperidine ring optionally having one or two substituents on the carbon atoms in the ring, the substituent is methyl or ethyl, and if there are two or more substituents, they may be the same or different; or $R^{31}$ and $R^{32}$ are linked to form a pyrrolidone ring or piperidinone ring optionally having one or two substituents on the carbon atoms in the ring, the substituent is methyl or ethyl, if there are two or more substituents, they may be the same or different, and $R^{33}$ is a hydrogen atom or a $C_{1-5}$ alkyl group.

More preferably, $R^{31}$, $R^{32}$, and $R^{33}$ are the same or different and each is a hydrogen atom or a $C_{1-3}$ alkyl group;

$R^{31}$ is a hydrogen atom or a $C_{1-3}$ alkyl group, and $R^{32}$ and $R^{33}$ are linked to form a pyrrolidine ring or a piperidine ring; or $R^{31}$ and $R^{32}$ are linked to form a pyrrolidone ring or a piperidinone ring, and RA is a hydrogen atom or a $C_{1-3}$ alkyl group.

Even more preferably, $R^{31}$, $R^{32}$, and $R^{33}$ are the same or different and each is a hydrogen atom or a $C_{1-3}$ alkyl group;

$R^{31}$ is a hydrogen atom ox a $C_{1-3}$ alkyl group, and $R^{32}$ and $R^{33}$ are linked to form a pyrrolidine ring; or $R^{31}$ and $R^{32}$ are linked to form a pyrrolidone ring, and $R^{33}$ is a $C_{1-3}$ alkyl group.

Particularly preferably, $R^{31}$, $R^{32}$, and $R^{33}$ are the same or different and each is a hydrogen atom, methyl, or ethyl;

$R^{31}$ is a hydrogen atom, methyl, or ethyl, and $R^{32}$ and $R^{33}$ are linked to form a pyrrolidine ring; or $R^{31}$ and $R^{32}$ are linked to form a pyrrolidone ring, and $R^{33}$ is a hydrogen atom, methyl, or ethyl.

Preferred specific examples of compound (3) include formic acid amide, N,N-dimethylacetamide, N, N-dimethylformamide, N-methyl-2-pyrrolidone, and N-ethyl-2-pyrrolidone.

For example, $R^{41}$, $R^{42}$, $R^{43}$, and $R^{44}$ are the same or different and each is a hydrogen atom or a $C_{1-10}$ alkyl group, or two of them are optionally linked to each other to form a ring optionally having one or more substituents. As is commonly understood by a person skilled in the art, when two groups are linked to each other to form a ring (e.g., a pyrrolidine ring), the other groups are hydrogen atoms or $C_{1-10}$ alkyl groups, as defined above. In the present specification, the same applies to any reference to a ring formed by two groups in formulas (3), (4-1), and (4-2).

Further, for example, $R^{41}$ and $R^{42}$ are the same or different and each is a $C_{1-5}$ alkyl group, and $R^{43}$ and $R^{44}$ are the same or different and each is a $C_{1-5}$ alkyl group, or are linked to each other to form a ring optionally having one or more substituents.

Preferably, $R^{41}$, $R^{42}$, $R^{43}$, and $R^{44}$ are the same or different and each is a hydrogen atom or a $C_{1-5}$ alkyl group; or $R^{41}$ and $R^{42}$ are the same or different and each is a hydrogen atom or a $C_{1-5}$ alkyl group, $R^{43}$ and $R^{44}$ are linked to each other to form a tetrahydropyrimidinone ring or imidazolidinone ring optionally having one or two substituents on the carbon atoms in the ring, and the substituent is methyl or ethyl.

More preferably, $R^{41}$, $R^{42}$, $R^{43}$, and $R^{44}$ are the same or different and each is a hydrogen atom or a $C_{1-3}$ alkyl group; or $R^{41}$ and $R^{42}$ are the same or different and each is a hydrogen atom or a $C_{1-3}$ alkyl group, and $R^{43}$ and $R^{44}$ are linked to each other to form a tetrahydropyrimidinone ring or an imidazolidinone ring.

Even more preferably, $R^{41}$, $R^{42}$, $R^{43}$, and $R^{44}$ are the same or different and each is a hydrogen atom, methyl, or ethyl; or $R^{41}$ and $R^{42}$ are the same or different and each is a hydrogen atom, methyl, or ethyl, and $R^{43}$ and $R^{44}$ are linked to each other to form a tetrahydropyrimidinone ring or an imidazolidinone ring.

Particularly preferably, $R^{41}$, $R^{42}$, $R^{43}$, and $R^{44}$ are the same and each is methyl or ethyl; or $R^{41}$ and $R^{42}$ are the same and each is methyl or ethyl, and $R^{41}$ and $R^{44}$ are linked to each other to form a tetrahydropyrimidinone ring.

Preferred specific examples of compound (4-1) include N,N'-dimethylpropylene urea, N,N'-dimethylethylene urea, tetraethyl urea, and tetramethyl urea.

For example, $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{49}$ and $R^{50}$ are optionally linked to each other to form a ring optionally having one or more substituents, or $R^{49}$ and $R^{50}$ are optionally linked to each other to form a ring optionally having one or more substituents.

Preferably, $R^{46}$ is a $C_{1-5}$ alkyl group, a 1-pyrrolidinyl group, a 1-piperidinyl group, a phenyl group optionally substituted with one, two, or three $C_{1-5}$ alkyl groups, or an amino group substituted with two $C_{1-5}$ alkyl groups, $R^{47}$, $R^{48}$, $R^{49}$, and $R^{50}$ are the same or different and each is a hydrogen atom or a $C_{1-4}$ alkyl group, or $R^{47}$ and $R^{48}$ are optionally linked to each other to form a pyrrolidine ring or a piperidine ring, $R^{47}$ and $R^{49}$ are optionally linked to each other to form a pyrrolidine ring or a piperidine ring, or $R^{49}$ and $R^{50}$ are optionally linked to each other to form a pyrrolidine ring or a piperidine ring. In this case, when the phenyl group is substituted with two or three $C_{1-4}$ alkyl groups, the alkyl groups may be the same or different, and two $C_{1-4}$ alkyl groups in the amino group may be the same or different.

More preferred is any of the following (1) to (3):
(1) $R^{46}$ is a $C_{1-4}$ alkyl group, a phenyl group optionally substituted with one, two, or three $C_{1-4}$ alkyl groups, an amino group substituted with two $C_{1-4}$ alkyl groups, or a 1-pyrrolidinyl group, $R^{47}$ and $R^{48}$ are linked to each other to form a pyrrolidine ring, and $R^{49}$ and $R^{50}$ are linked to each other to form a pyrrolidine ring;
(2) $R^4$ is a $C_{1-4}$ alkyl group, a phenyl group optionally substituted with one, two, or three $C_{1-4}$ alkyl groups, an amino group substituted with two $C_{1-4}$ alkyl groups, or a 1-piperidinyl group, $R^{47}$ and $R^{49}$ are linked to each other to form a piperidine ring, and $R^{49}$ and $R^{50}$ are linked to each other to form a piperidine ring; and
(3) $R^{46}$ is a $C_{1-4}$ alkyl group, a phenyl group optionally substituted with one, two, or three $C_{1-4}$ alkyl groups, or an amino group substituted with two $C_{1-4}$ alkyl groups, $R^{47}$, $R^{48}$, $R^{49}$, and $R^{50}$ are the same or different and each is a hydrogen atom or a $C_{1-4}$ alkyl group, or $R^{48}$ and $R^{50}$ are optionally linked to each other to form a pyrrolidine ring or a piperidine ring.

Even more preferred is any of the following (1) to (5):
(1) $R^4$ is a phenyl group optionally substituted with one, two, or three $C_{1-4}$ alkyl groups, an amino group substituted with two $C_{1-4}$ alkyl groups, or a 1-pyrrolidinyl group, $R^{47}$ and $R^{48}$ are linked to each other to form a pyrrolidine ring, and $R^{49}$ and $R^{50}$ are linked to each other to form a pyrrolidine ring;
(2) $R^{46}$ is a phenyl group optionally substituted with one, two, or three $C_{1-4}$ alkyl groups, an amino group substituted with two $C_{1-4}$ alkyl groups, or a 1-piperidinyl group, $R^{47}$ and $R^{48}$ are linked to each other to form a piperidine ring, and $R^{49}$ and $R^{50}$ are linked to each other to form a piperidine ring;
(3) $R^{46}$ is an amino group substituted with two same $C_{1-4}$ alkyl groups, and —$NR^{47}R^{48}$ and —$NR^{49}R^{50}$ are the same groups as the amino group;
(4) $R^{46}$ is a phenyl group, and $R^{47}$, $R^{48}$, $R^{49}$, and $R^{50}$ are the same or different and each is a $C_{1-4}$ alkyl group; and
(5) $R^{46}$ is a $C_{1-4}$ alkyl group, $R^{47}$, $R^{48}$, $R^{49}$, and $R^{50}$ are the same or different and each is a $C_{1-4}$ alkyl group, or $R^{48}$ and $R^{50}$ are optionally linked to each other to form a pyrrolidine ring.

Particularly preferred is any of the following (1) to (6):
(1) $R^{46}$ is a 1-pyrrolidinyl group, $R^{47}$ and $R^{48}$ are linked to each other to form a pyrrolidine ring, and $R^{49}$ and $R^{50}$ are linked to each other to form a pyrrolidine ring;
(2) $R^{46}$ is a 1-piperidinyl group, $R^{47}$ and $R^{48}$ are linked to each other to form a piperidine ring, and $R^{49}$ and $R^{50}$ are linked to each other to form a piperidine ring;
(3) $R^{46}$ is dimethylamino, diethylamino, dipropylamino, or diisopropylamino, and —$NR^{47}R^{48}$ and —$NR^{49}R^{50}$ are the same groups as the amino;
(4) $R^{46}$ is a phenyl group, and $R^{47}$, $R^{48}$, $R^{49}$, and $R^{50}$ are the same and each is methyl, ethyl, propyl, or isopropyl;
(5) $R^{46}$ is methyl or ethyl, $R^{47}$ and $R^{49}$ are the same and each is methyl, ethyl, propyl, or isopropyl, and $R^{48}$ and $R^{50}$ are linked to each other to form a pyrrolidine ring; and
(6) $R^{46}$, is methyl or ethyl, and $R^{47}$, $R^{48}$, $R^{49}$, and $R^{50}$ are the same and each is methyl, ethyl, propyl, or isopropyl.

Preferred specific examples of compound (4-2) include hexamethylphosphoric triamide (in the present specification, also referred to as "HMPA"), 1,2,3-trimethyl-1,3,2-diazaphospholidine 2-oxide, methylbis(dimethylamino)phosphine oxide, phenylbis(dimethylamino)phosphine oxide, tripyrrolidyl phosphine oxide, and methylbis(diethylamino) phosphine oxide.

In an embodiment of the present disclosure, preferred specific examples of compound (4) include at least one compound selected from the group consisting of N,N'-dimethylpropylene urea, N,N'-dimethylethylene urea, tetramethyl urea, tetraethyl urea, 1,2,3-trimethyl-1,3,2-diazaphospholidine 2-oxide, methylbis(dimethylamino)phosphine oxide, phenylbis(dimethylamino)phosphine oxide, tripyrrolidyl phosphine oxide, and methylbis(diethylamino) phosphine oxide.

Step A

In step A, compound (2) is preferably supplied as gas into the reaction system. The amount of compound (2) in the gas may be within the range of, for example, 70 mass % to 99.8 mass %, preferably 90 mass % to 99.8 mass %, more preferably 92 mass % to 99.8 mass %, and particularly preferably 95 mass % to 99.8 mass %, based on the weight of the gas.

The amount of compound (3) used in step A may be preferably within the range of 0.05 to 10 mol, more preferably 0.08 to 5 mol, and even more preferably 0.1 to 2 mol, per mol of compound (2).

The amount of compound (4) used in step A may be preferably within the range of 0.001 to 0.3 mol, more preferably 0.005 to 0.1 mol, and even more preferably 0.005 to 0.05 mol, per mol of compound (2).

When compound (4-1) is used in step A, the amount of compound (4-1) may be preferably within the range of 0.001 to 0.3 mol, more preferably 0.005 to 0.1 mol, and even more preferably 0.005 to 0.05 mol, per mol of compound (2).

When compound (4-2) is used in step A, the amount of compound (4-2) may be preferably within the range of 0.005 to 0.05 mol, more preferably 0.005 to 0.045 mol, and even more preferably 0.005 to 0.04 mol, per mol, of compound (2). When the amount of compound (4-2) used is within this range, the selectivity of compound 1 is greatly improved, the yield and purity of compound 1 are increased, and the purification of compound 1 is simplified. Further, the product purified in step A (e.g., product liquid) can also be used directly for the synthesis of compound 5.

Step A is preferably performed in the presence of an organic solvent. Compounds (3) and (4) are considered to act as reactants in step A. Compounds (3) and (4) are excluded from the organic solvent in step A.

Examples of organic solvents include aromatic solvents, ester solvents, ketone solvents, saturated hydrocarbon solvents, nitrile solvents, ether solvents, sulfoxide solvents, and halogenated hydrocarbon solvents. These organic solvents can be used singly or in combination of two or more.

Preferred examples of organic solvents include ether solvents, ester solvents, halogenated hydrocarbon solvents, and nitrile solvents.

Preferred specific examples of aromatic solvents include benzene, toluene, and xylene.

Preferred specific examples of ester solvents include methyl formate, ethyl formate, methyl acetate, ethyl acetate, isopropyl acetate, methyl propionate, ethyl propionate, and n-butyl acetate.

Preferred specific examples of ketone solvents include acetone, methyl ethyl ketone, methyl isobutyl ketone, and cyclohexanone.

Preferred specific examples of saturated hydrocarbon solvents include n-pentane, n-hexane, cyclohexane, and n-heptane.

Preferred specific examples of nitrile solvents include 1,4-dicyanobutane, acetonitrile, and benzonitrile.

Preferred specific examples of ether solvents include diethylene glycol dimethyl, ether, triethylene glycol dimethyl ether, tetraethylene glycol dimethyl ether, diethyl ether, diisopropyl ether, dioxane, tetrahydrofuran, 1,2-dimethoxyethane, and crown ether.

Preferred specific examples of sulfoxide solvents include dimethyl sulfoxide and sulfolane.

Preferred specific examples of halogenated hydrocarbon solvents include methylene chloride, chloroform, carbon tetrachloride, 1,2-dichloroethane, 1,2-dichlorobenzene, chlorobenzene, and perfluorohexane.

Preferred specific examples of organic solvents include ethyl acetate, diethylene glycol dimethyl ether, triethylene glycol dimethyl ether, tetraethylene glycol dimethyl ether, 1,4-dicyanobutane, methylene chloride, chloroform, tetrahydrofuran, perfluorohexane, and acetonitrile.

The amount of the organic solvent used in step A may be an amount that can function as a solvent, based on common technical knowledge etc. The amount of the organic solvent used in step A may be preferably within the range of 0.1 to 50 mol, more preferably 0.1 to 20 mol, and even more preferably 0.1 to 10 mol, per mol of compound (2).

The reaction temperature in step A may be preferably within the range of −30 to 40° C., more preferably −30 to 30° C., and even more preferably −20 to 30° C. As the reaction temperature in step A decreases, the selectivity of compound (1) tends to increase. As the reaction temperature in step A increases, the reactivity tends to increase.

The reaction time in step A may be preferably within the range of 0.5 hours to 48 hours, more preferably 0.5 hours to 24 hours, and even more preferably 0.5 hours to 12 hours.

The reaction in step A may be performed in the presence or absence of an inert gas (e.g., nitrogen gas), and preferably in the absence of an inert gas.

Step A can be performed under reduced pressure, atmospheric pressure, or increased pressure.

In step A, compounds (2), (3), and (4) may be reacted in an organic solvent. Step A is preferably performed by mixing compound (3), compound (4), and an organic solvent, cooling the mixture (e.g., −10° C.), and adding compound (2) thereto.

Compound (1) produced in step A can be isolated or purified, if desired, by a conventional method, such as extraction, dissolution, concentration, precipitation, dehydration, adsorption, distillation, rectification, or chromatography, or a combination of these methods.

Step A preferably does not include CsF (cesium fluoride). Step A more preferably does not include at least one fluorine compound (9) (in the present specification, also referred to as "compound (9)") selected from the group consisting of:

a compound represented by formula (9-1):

(9-1)

wherein M is a metal atom, n is 0 or 1, and the sum of the valence number of M and n is m (in the present specification, also referred to as "compound (9-1)");

a compound represented by formula (9-2):

(9-2)

wherein L is a nitrogen atom or a phosphorus atom, and $R^{91}$ are the same or different and each is a $C_{1-5}$ alkyl group (in the present specification, also referred to as "compound (9-2)"); and hydrofluoric acid or a salt thereof.

For example, M is an alkali metal atom, and n is 0 or 1; or M is an alkaline earth metal atom, and n is 0.

For example, M is a sodium atom, a potassium atom, or a cesium atom, and n is 0 or 1; or M is a calcium atom, and n is 0.

For example, M is a potassium atom or a cesium atom, and n is 0 or 1; or M is a calcium atom, and n is 0.

Specific examples of compound (9-1) include cesium fluoride, potassium hydrogen fluoride, calcium fluoride, sodium fluoride, potassium fluoride, and sodium hydrogen fluoride.

For example, L is a nitrogen atom or a phosphorus atom, and $R^{91}$ are the same or different and each is a $C_{1-4}$ alkyl group.

For example, L is a nitrogen atom or a phosphorus atom, and $R^{91}$ are the same and each is a $C_{1-4}$ alkyl group.

For example, L is a nitrogen atom or a phosphorus atom, and $R^{91}$ are the same and each is a linear $C_{1-6}$ alkyl group.

For example, L is a nitrogen atom or a phosphorus atom, and $R^{91}$ are the same and each is methyl, ethyl, or n-butyl.

Specific examples of compound (9-2) include tetrabutylammonium fluoride, tetraethylammonium fluoride, tetramethylammonium fluoride, tetrabutylphosphonium fluoride, and triethylmethylammonium fluoride.

Salts of hydrofluoric acid include amine salts, ammonium salts, imidazolium salts, pyridinium salts, phosphonium salts, and the like. These salts may contain one or more substituents. If there are two or more substituents, they may be the same or different.

The amine salt of hydrofluoric acid may be substituted. The number of substituents is, for example, 1 to 3, 2 or 3, or 3. When there are two or more substituents, they may be the same or different. Examples of substituents include Ca, alkyl groups, C-alkyl groups, and $C_{1-4}$ alkyl groups.

Examples of amine salts of hydrofluoric acid include tri-$C_{1-4}$ alkylamine hydrofluoride (the number of HF$^-$ may be any integer of 1 to 7).

Specific examples of amine salts of hydrofluoric acid include trimethylamine hydrofluoride (the number of HF$^-$ may be any integer of 1 to 7, for example, 3, 4, or 5) and triethylamine hydrofluoride (the number of HF$^-$ may be any integer of 1 to 7, for example, 3, 4, or 5).

When the ammonium salt of hydrofluoric acid is substituted, the number of substituents is, for example, 1 to 4, 2 to 4, 3 or 4, or 4. When there are two or more substituents, they may be the same or different. Examples of substituents include $C_{1-10}$ alkyl groups, and may be $C_{1-5}$ alkyl groups or $C_{1-4}$ alkyl groups.

Specific examples of ammonium salts of hydrofluoric acid include ammonium fluoride, ammonium hydrogen fluoride, and tetra-$C_{1-4}$ alkylammonium fluoride.

Specific examples of ammonium salts of hydrofluoric acid include ammonium fluoride, ammonium hydrogen fluoride, tetramethylammonium fluoride, tetraethylammonium fluoride, and tetrabutylammonium fluoride.

The imidazolium salt of hydrofluoric acid may be such that the nitrogen atoms in the imidazolium ring are substituted. The number of substituents is, for example, 1 to 3, 2 or 3, or 2. When there are two or more substituents, they may be the same or different. Examples of substituents include $C_{1-10}$ alkyl groups (e.g., methyl, ethyl, n-propyl, isopropyl, n-butyl, and tert-butyl), cyclohexyl, vinyl, and allyl. The substituents may be $C_{1-3}$ alkyl groups.

Specific examples of imidazolium salts of hydrofluoric acid include 1-methyl-3-methylimidazolium fluoride and 1-ethyl-3-methylimidazolium fluoride.

The pyridinium salt of hydrofluoric acid may be substituted. The number of substituents is, for example, 1 to 3, or 1 or 2. When there are two or more substituents, they may be the same or different. Examples of substituents include $C_{1-10}$ alkyl groups. The substituents may be $C_{1-5}$ alkyl groups or $C_{1-4}$ alkyl groups.

Specific examples of pyridinium salts of hydrofluoric acid include pyridinium poly(hydrogen fluoride) (the number of $HF^-$ may be any integer of 1 to 9, for example, 1 or 9).

The phosphonium salt of hydrofluoric acid may be substituted. The number of substituents is, for example, 1 to 4, 3 or 4, or 4. Examples of substituents include $C_{1-4}$ alkyl groups, optionally substituted phenyl, and optionally substituted benzyl. The substituents may be $C_{1-5}$ alkyl groups or C alkyl groups.

Specific examples of phosphonium salts of hydrofluoric acid include tetramethylphosphonium hydrofluoride, tetraethylphosphonium hydrofluoride, tetrapropylphosphonium hydrofluoride, tetrabutylphosphonium hydrofluoride, tetraoctylphosphonium hydrofluoride, trimethylethylphosphonium hydrofluoride, triethylmethylphosphonium hydrofluoride, hexyltrimethylphosphonium hydrofluoride, trimethyloctylphosphonium hydrofluoride, triethyl (methoxymethyl)phosphonium hydrofluoride, and triethyl (methoxymethyl)phosphonium hydrofluoride.

In an embodiment of the present disclosure, specific examples of compound (9) include at least one fluorine compound selected from the group consisting of cesium fluoride, potassium hydrogen fluoride, calcium fluoride, sodium fluoride, potassium fluoride, sodium hydrogen fluoride, tetrabutylammonium fluoride, tetraethylammonium fluoride, tetramethylammonium fluoride, tetrabutylphosphonium fluoride, triethylmethylammonium fluoride, triethylamine trihydrofluoride, triethylamine pentahydrofluoride, triethylamine heptahydrofluoride, pyridinium poly(hydrogenfluoride), pyridine monohydrofluoride, pyridinium poly (hydrogenfluoride), pyridine nonahydrofluoride, ammonium hydrogen fluoride, and ammonium fluoride.

In a conventional method for producing compound (1) by reacting hexafluoropropylene oxide with N,N-dimethylformamide at 0° C. (first reaction), and then heating the reactant at 140° C. in diethylene glycol dimethyl ether in the presence of cesium fluoride (second reaction), a large amount of difluoroamine is produced as a by-product during the first reaction. Since difluoroamine converts the target compound (1) into another compound, it is necessary to trap and remove difluoroamine with HCl gas, which is harmful to human health, before the second reaction. In step A of the present disclosure, the use of a solvent eliminates the need to trap difluoroamine with HCl gas, because difluoroamine is transferred to the solvent and the contact between difluoroamine and compound (1) is suppressed.

In the method disclosed in PTL 1, fluorine gas, which is difficult to handle and dangerous, is used in the production of 3,5,5,6-tetrafluoro-3,6-bis(trifluoromethyl)-1,4-dioxane-2-one. Further, in the method disclosed in PTL 1, 3,5,5,6-tetrafluoro-3,6-bis(trifluoromethyl)-1,4-dioxane-2-one is produced as a mixture and is difficult to purify. In contrast, step A of the present disclosure does not require the use of fluorine gas, and the product liquid obtained in step A is easy to purify, and can be purified by liquid separation, for example.

Step B

The method for producing the compound represented by formula (1) of the present disclosure may further comprise step B of performing liquid separation, in addition to step A. The reaction liquid produced in step A can be composed of two layers, an upper liquid layer and a lower liquid layer, one of which (preferably the lower liquid layer) contains compound (1). Therefore, the liquid layer containing the target compound (1) can be easily obtained by separating the reaction liquid.

The method for isolating compound (1) from the liquid layer may be a conventional method, such as extraction, dissolution, concentration, precipitation, dehydration, adsorption, distillation, rectification, or chromatography, or a combination of these methods. Since the liquid layer containing compound (1) obtained in step B contains few foreign compounds with a boiling point close to that of compound (1), compound (1) can be easily obtained by distilling the liquid layer. The liquid layer may be directly used for the synthesis of compound (5).

Methods for Producing Compound Represented by Formula (5)

An embodiment of the present disclosure is a method for producing a compound represented by formula (5):

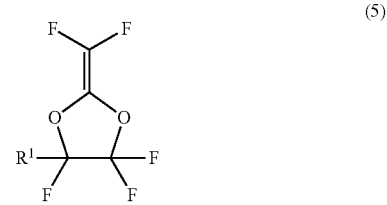

wherein $R^1$ is a fluorine atom or a fluoroalkyl group (in the present specification, also referred to as "compound (5)").

This method comprises:
step C of heating the compound represented by formula (1) produced in step A or B in the presence of at least one fluorine compound (9) (in the present specification, also referred to as compound (9)) selected from the group consisting of:
a compound represented by formula (9-1):

$$MH_nF_n \qquad (9\text{-}1)$$

wherein M is a metal atom, n is 0 or 1, and the sum of the valence number of M and n is m;
a compound represented by formula (9-2):

$$LR^{91}{}_4F \qquad (9\text{-}2)$$

wherein L is a nitrogen atom or a phosphorus atom, and $R^{91}$ are the same or different and each is a $C_{1-5}$ alkyl group; and
hydrofluoric acid or a salt thereof,
to produce a compound represented by formula (6):

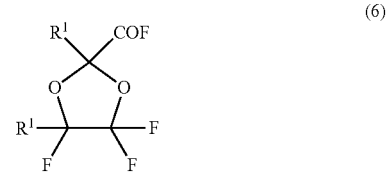

wherein R¹ are as defined above (in the present specification, also referred to as "compound (6)");

step D of reacting the compound represented by formula (6) with a base (in the present specification, also referred to as "base (d)") to produce a compound represented by formula (8):

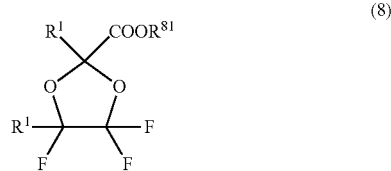

(8)

wherein R⁸¹ is a group corresponding to the base, and R¹ are as defined above; and step E of heating the compound represented by formula (8) (in the present specification, also referred to as "compound (8)") to produce the compound represented by formula (5).

Compound (8) is a carboxylic acid salt of compound (6), corresponding to base (d).

R⁸¹ is preferably an alkali metal atom, an alkaline earth metal atom, pyridinium, ammonium, or amino optionally substituted with an organic group; more preferably a potassium atom, a sodium atom, or ammonium; and particularly preferably a sodium atom or a potassium atom.

In the present specification, except for using the compound of formula (1) produced in step A or B as a raw material in step C, steps C, D, E, and F may be performed by a known method, for example, according to the method disclosed in JP-2005-002014A, U.S. Pat. No. 3,308,107B, or U.S. Pat. No. 6,664,431B. These publications are incorporated herein by reference.

Step C

In step C, compound (1) produced in step A or B is isomerized by heating in the presence of compound (9) to produce compound (6).

In step C, compound (1) produced in step A or B may be used after isolation, or the liquid layer of the reaction liquid containing compound (1) obtained in step B may be used.

For the details of compound (9) in step C, the description of the details of compound (9) in step (A) is applied, unless otherwise specified.

The amount of compound (9) used in step C may be preferably within the range of 0.001 to 10 mol, more preferably 0.002 to 5.0 mol, and even more preferably 0.006 to 1.0 mol, per mol of compound (1).

Step C may be preferably performed in an organic solvent. Examples and preferred examples of organic solvents are the same as those mentioned above. Preferred specific examples of organic solvents include diethylene glycol dimethyl ether, triethylene glycol dimethyl ether, tetraethylene glycol dimethyl ether, 1,4-dicyanobutane, acetonitrile, 1,2-dimethylether, tetrahydrofuran, and dimethylsulfoxide.

The amount of the organic solvent used in step C may be an amount that can function as a solvent, based on common technical knowledge etc.

The reaction temperature in step C may be preferably within the range of 50 to 300° C., more preferably 50 to 200° C., and even more preferably 100 to 180° C.

The reaction time in step C may be preferably within the range of 0.5 hours to 60 hours, more preferably 1 hour to 24 hours, and even more preferably 2 hours to 24 hours.

Compound (6) produced in step C can be isolated or purified, if desired, by a conventional method, such as extraction, dissolution, concentration, precipitation, dehydration, adsorption, distillation, rectification, or chromatography, or a combination of these methods.

Step D

In step D, compound (6) is reacted with base (d) to produce compound (8). Compound (8) is a carboxylic acid salt of compound (6), corresponding to base (d).

Base (d) is, for example, at least one member selected from the group consisting of (1)acetate, carbonate, hydrogen carbonate, phosphate, hydrogen phosphate, alkoxide salts, hydroxide salts, hydride salts, ammonium salts, or amide salts of alkali or alkaline earth metals, (2)alkali metals, and (3) amines.

Examples of alkoxide salts include sodium methoxide, sodium ethoxide, sodium butoxide, potassium methoxide, potassium ethoxide, potassium butoxide, lithium methoxide, and lithium ethoxide.

Examples of hydroxide salts include sodium hydroxide, potassium hydroxide, lithium hydroxide, rubidium hydroxide, cesium hydroxide, magnesium hydroxide, calcium hydroxide, and barium hydroxide.

Examples of hydride salts include sodium hydride, potassium hydride, lithium hydride, and calcium hydride.

Examples of alkali metals include sodium, potassium, and lithium.

Examples of amines include aliphatic amines, alicyclic amines, aromatic amines, and heterocyclic amines. The amines may be preferably tertiary amines.

Base (d) is preferably at least one member selected from the group consisting of sodium methoxide, sodium hydroxide, potassium hydroxide, sodium carbonate, potassium carbonate, sodium hydrogen carbonate, potassium hydrogen carbonate, cesium carbonate, and ammonia.

Base (d) is more preferably at least one member selected from the group consisting of potassium hydroxide, sodium hydroxide, potassium hydrogen carbonate, sodium hydrogen carbonate, potassium carbonate, and sodium carbonate.

Step D may be preferably performed in an organic solvent. Examples and preferred examples of organic solvents are the same as those mentioned above. Preferred specific examples of organic solvents include methanol, ethanol, diethylene glycol dimethyl ether, triethylene glycol dimethyl, ether, tetraethylene glycol dimethyl ether, 1,4-dicyanobutane, 1,2-dimethylether, tetrahydrofuran, and acetonitrile.

The amount of base (d) used in step D may be preferably within the range of 0.05 to 10 mol, more preferably 0.1 to 10 mol, and even more preferably 0.1 to 5 mol, per mol of compound (6).

The amount of the organic solvent used in step D may be an amount that can function as a solvent, based on common technical knowledge etc.

The reaction temperature in step D may be preferably within the range of −50 to 120° C., more preferably −20 to 100° C., and even more preferably −10 to 70° C.

The reaction time in step D may be preferably within the range of 0.1 hours to 24 hours, more preferably 0.1 hours to 12 hours, and even more preferably 0.1 hours to 6 hours.

Compound (8) produced in step D can be isolated or purified, if desired, by a conventional method, such as extraction, dissolution, concentration, precipitation, dehydration, adsorption, distillation, rectification, or chromatography, or a combination of these methods.

In step E, compound (8) is thermally decomposed by heating to produce compound (5). Compound (5) is useful as an intermediate etc. for the production of raw materials of resin materials.

Step E may be performed in an organic solvent or without a solvent. Examples and preferred examples of organic solvents are the same as those mentioned above. Preferred specific examples of organic solvent include ethyl acetate, butyl acetate, propyl acetate, methyl propionate, ethyl propionate, 1,2-dimethoxyethane, diethylene glycol dimethyl ether, triethylene glycol dimethyl ether, tetraethylene glycol dimethyl ether, 1,4-dicyanobutane, and acetonitrile.

The amount of the organic solvent used in step E may be an amount that can function as a solvent, based on common technical knowledge etc.

When a solvent is contained, the reaction temperature in step E may be preferably within the range of 100 to 400° C., more preferably 100 to 300° C., and even more preferably 100 to 200° C. When a solvent is not contained, the reaction temperature in step E may be preferably within the range of 100 to 400° C., more preferably 150 to 400° C., and even more preferably 150 to 350° C.

The reaction time in step E may be preferably within the range of 0.1 hours to 24 hours, more preferably 0.1 hours to 12 hours, and even more preferably 0.1 hours to 6 hours.

The reaction in step E may be performed in the presence or absence of an inert gas (e.g., nitrogen gas), and preferably in the absence of an inert gas.

Step E can be performed under reduced pressure, atmospheric pressure, or increased pressure.

Compound (5) produced in step E can be isolated or purified, if desired, by a conventional method, such as extraction, dissolution, concentration, precipitation, dehydration, adsorption, distillation, rectification, or chromatography, or a combination of these methods.

An embodiment of the present disclosure is a method for producing the compound represented by formula (5), the method comprising, in place of step D:

step D1 of reacting the compound represented by formula (6) with water or alkyl alcohol to produce a compound represented by formula (7):

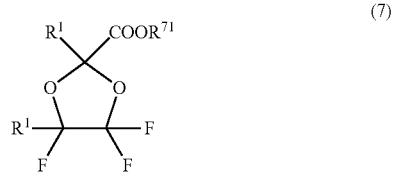

(7)

wherein $R^{71}$ is a hydrogen atom or an alkyl group, and $R^1$ are as defined above (in the present specification, also referred to as "compound (7)"); and step D2 of reacting the compound represented by formula (7) with a base (in the present specification, also referred to as "base (d2)") to produce the compound represented by formula (8).

$R^{71}$ is preferably a hydrogen atom or a linear or branched $C_{1-10}$ alkyl group, more preferably a hydrogen atom or a linear or branched $C_{1-5}$ alkyl group, even more preferably a linear or branched $C_{1-4}$ alkyl group, particularly preferably methyl, ethyl, n-propyl, isopropyl, n-butyl, sec-butyl, or tert-butyl, and further particularly preferably methyl or ethyl.

Step D1

In step D1, compound (6) Is reacted with water or alkyl alcohol for conversion to a corresponding carboxylic acid or alkyl ester, thereby producing compound (7).

In step D1, compound (6) may be isolated, or the product liquid containing compound (6) produced in step C may be used as it is. The use of this product liquid is preferable because it is advantageous that the purification of compound (6) is not necessary.

The alkyl alcohol is preferably a linear or branched $C_{1-10}$ alkyl alcohol, more preferably a linear or branched $C_{1-5}$ alkyl alcohol, even more preferably a linear or branched $C_{1-4}$ alkyl alcohol, particularly preferably methanol, ethanol, n-propanol, isopropanol, n-butyl alcohol, sec-butyl alcohol, or tert-butyl alcohol, and further particularly preferably methanol or ethanol.

The amount of water, alkyl alcohol, or mixture of water and alcohol to be used in step D1 may be preferably within the range of 0.1 to 50 mol, more preferably 0.2 to 20 mol, and even more preferably 0.5 to 10 mol, per mol of compound (6).

In step D1, in addition to water and alkyl alcohol, other organic solvents may be further used. Examples and preferred examples of organic solvents are the same as those mentioned above. Specific examples of such organic solvents include 1,2-dimethoxyethane, diethylene glycol dimethyl ether, triethylene glycol dimethyl ether, tetraethylene glycol dimethyl ether, 1,4-dicyanobutane, and acetonitrile. The amount of the organic solvent can be preferably within the range of 0.01 to 50 mol, and more preferably 0.1 to 50 mol, per mol of compound (6).

The reaction temperature in step D1 may be preferably within the range of −50 to 50° C., more preferably −20 to 30° C., and even more preferably −20 to 20° C.

The reaction time in step D1 may be preferably within the range of 0.1 hours to 24 hours, more preferably 0.1 hours to 12 hours, and even more preferably 0.1 hours to 6 hours.

The reaction in step D1 may be performed in the presence or absence of an inert gas (e.g., nitrogen gas), and preferably in the absence of an inert gas.

Step D1 can be performed under reduced pressure, atmospheric pressure, or increased pressure.

Compound (7) produced in step D1 can be isolated or purified, if desired, by a conventional method, such as extraction, dissolution, concentration, precipitation, dehydration, adsorption, distillation, rectification, or chromatography, or a combination of these methods.

Compound (6) is reacted with alkyl alcohol to produce compound (7) in the reaction liquid, water is added to the reaction liquid, and the resulting organic layer is collected and distilled, whereby compound (7) can be easily purified, which is preferable.

Step D2

In step D2, compound (7) is reacted with base (d2) to produce compound (8). For the details of base (d2) in step D2, the description of the details of the base in step D is applied, unless otherwise specified.

The amount of base (d2) used in step D2 may be preferably within the range of 0.1 to 20 mol, more preferably 0.5 to 15 mol, and even more preferably 1 to 10 mol, per mol of compound (7).

Step D2 is preferably performed in the presence of an organic solvent. Examples and preferred examples of organic solvents are the same as those mentioned above.

The organic solvent is preferably methanol, ethanol, 1,2-dimethoxyethane, diethylene glycol dimethyl ether, triethylene glycol dimethyl ether, tetraethylene glycol dimethyl ether, 1,4-dicyanobutane, acetonitrile, or tetrahydrofuran. These organic solvents may be used singly or as a mixture of two or more.

The reaction temperature in step D2 may be preferably within the range of −50 to 120*C, more preferably −20 to 100° C., and even more preferably −10 to 70° C.

The reaction time in step D2 may be preferably within the range 0.1 hours to 24 hours, more preferably 0.1 hours to 12 hours, and even more preferably 0.1 hours to 6 hours.

The reaction in step D2 may be performed in the presence or absence of an inert gas (e.g., nitrogen gas), and preferably in the absence of an inert gas.

Step D2 can be performed under reduced pressure, atmospheric pressure, or increased pressure.

In step D2, compound (8) can precipitate as a solid in the solvent. When a solid precipitates, compound (8) can be easily isolated by removing the solvent. The solvent can be removed by any known method.

An embodiment of the present disclosure is a method for producing the compound represented by formula (5), the method further comprising step D1a of purifying the product (preferably product liquid) of step D1 to obtain the compound represented by formula (7). The purified compound (7) may be subjected to step D2.

Step D1a

In step D1a, the product (e.g., reaction liquid) produced in step D1 is purified to obtain compound (7). Compound (7) can be isolated or purified by a conventional, method, such as extraction, dissolution, concentration, precipitation, dehydration, adsorption, distillation, rectification, or chromatography, or a combination of these methods. Preferably, the organic layer of the reaction liquid produced in step D1 is purified, more preferably by distillation, to easily obtain compound (7). The organic layer often contains no or only small amounts of other substances with a boiling point near the boiling point of compound (7), and is thus suitable for purification by distillation.

An embodiment of the present disclosure is a method for producing the compound represented by formula (5), the method comprising, in place of steps D and E, step F of heating the compound represented by formula (6) in the presence of a base (in the present specification, also referred to as "base (f)") to produce the compound represented by formula (5).

Step F

In step F, compound (6) is heated in the presence of base (f) to produce the compound represented by formula (5). Step F may be performed by a known method, for example, according to the method disclosed in U.S. Pat. No. 3,308,107B or U.S. Pat. No. 6,664,431B. These publications are incorporated herein by reference.

In step F, compound (6) may be isolated, or the product liquid containing compound (6) produced in step C may be used as it is. The use of this product liquid is preferable because it is advantageous that the purification of compound (6) is not necessary.

For the details of base (f) in step F, the description of the details of the base in step U is applied, unless otherwise specified.

Base (f) is preferably a hydroxide, halide, carbonate, or hydrogen carbonate of an alkali metal, or ammonia. The alkali metal halide may be carried on a carrier, such as activated carbon or inorganic oxide.

Base (f) is more preferably at least one member selected from the group consisting of sodium hydroxide, potassium hydroxide, sodium carbonate, potassium carbonate, cesium carbonate, sodium hydrogen carbonate, potassium hydrogen carbonate, ammonia, potassium fluoride, sodium fluoride, cesium fluoride, sodium chloride, and potassium iodide.

Base (f) is even more preferably at least one member selected from the group consisting of potassium hydroxide, potassium hydrogen carbonate, potassium carbonate, sodium carbonate, potassium fluoride, sodium fluoride, cesium fluoride, sodium chloride, and potassium iodide.

The carrier of base (f) is preferably activated carbon, an alkali metal oxide, an alkaline earth metal oxide, zinc oxide, aluminum oxide, nickel oxide, or silicon dioxide.

The carrier of base (f) is more preferably at least one member selected from the group consisting of alkaline earth metal oxides, aluminum oxide, and silicon dioxide.

Specific examples of alkali metal oxides include lithium oxide, sodium oxide, potassium oxide, rubidium oxide, and cesium oxide.

Specific examples of alkaline earth metal oxides include magnesium oxide, calcium oxide, and barium oxide.

Step F may be performed in an organic solvent or without a solvent. Examples and preferred examples of organic solvents are the same as those mentioned above. Preferred specific examples of organic solvents include ethyl acetate, propyl acetate, butyl acetate, methyl propionate, ethyl propionate, 1,2-dimethoxyethane, diethylene glycol dimethyl ether, triethylene glycol dimethyl ether, tetraethylene glycol dimethyl ether, 1,4-dicyanobutane, tetrahydrofuran, and acetonitrile.

The amount of base (f) used in step F may be preferably within the range of 0.1 to 200 mol, more preferably 0.5 to 100 mol, and even more preferably 1 to 50 mol, per mol of compound (6).

The amount of the inorganic oxide used in step F may be preferably within the range of 0.2 to 400 mol, more preferably 1 to 200 mol, and even more preferably 2 to 100 mol, per mol of compound (6).

The amount of the organic solvent used in step F may be an amount that can function as a solvent, based on common technical knowledge etc.

When a solvent is contained, the reaction temperature in step F may be preferably within the range of 80 to 400° C., more preferably 100 to 350° C., and even more preferably 100 to 300° C. When a solvent is not contained, the reaction temperature in step F may be preferably within the range of 100 to 400° C., more preferably 150 to 400° C., and even more preferably 150 to 350° C.

The reaction time in step F may be preferably within the range of 0.01 hours to 24 hours, more preferably 0.01 hours to 12 hours, and even more preferably 0.01 hours to 6 hours.

The reaction in step F may be performed in the presence or absence of an inert gas (e.g., nitrogen gas), and preferably in the absence of an inert, gas.

Step F can be performed under reduced pressure, atmospheric pressure, or increased pressure.

Compound (5) produced in step F can be isolated or purified, if desired, by a conventional method, such as extraction, dissolution, concentration, precipitation, dehydration, adsorption, distillation, rectification, or chromatography, or a combination of these methods.

Composition

An embodiment of the present disclosure is a composition comprising the compound represented by formula (1), and further comprising, based on 100 parts by mass of the compound represented by formula (1), 0.00001 to 1 part by mass of a compound represented by formula (10):

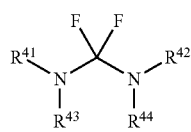

wherein $R^{41}$, $R^{42}$, $R^{43}$, and $R^{44}$ are the same or different and each is a hydrogen atom or an alkyl group, or two of them are optionally linked to each other to form a ring optionally having one or more substituents (in the present specification, also referred to as "compound (10)"), and/or 0.00001 to 1 part by mass of a compound represented by formula (11):

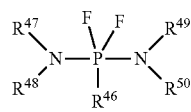

wherein $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{48}$ and $R^{50}$ are optionally linked to each other to form a ring optionally having one or more substituents, or $R^{49}$ and $R^{50}$ are optionally linked to each other to form a ring optionally having one or more substituents (in the present specification, also referred to as "compound (11)").

The method for producing the compound represented by formula (1) of the present disclosure can also produce the composition described above. The composition may further contain compounds (3), (4-1), and (4-2), a polymerization inhibitor, water, or a polar solvent.

The amount of each of the components contained in the composition can be adjusted by setting the reaction conditions (e.g., temperature, time, type and amount of raw material, type and amount of solvent, and type and amount of catalyst). Further, the amounts of the various components can be adjusted by purification after the production of compound (1).

Compounds (10) and (11) are produced, for example, by fluorinating compounds (4-1) and (4-2), respectively, in the production process of compound (1). For the details of $R^{41}$ to $R^{44}$ in formula (10) and $R^{46}$ to $R^{50}$ in formula (11) in the composition, the description of the details of $R^{41}$ to $R^{46}$ in formula (4-1) and $R^{45}$ to $R^{50}$ in formula (4-2) is applied, respectively. Further, the fluorides mentioned above as preferred specific examples of compounds (4-1) and (4-2) are preferred specific examples of compounds (10) and (11), respectively.

The quantitative ratio of compound (10) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (1).

The quantitative ratio of compound (11) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (1).

The composition may contain either or both of compounds (10) and (11). The composition preferably contains 0.00001 to 0.8 parts by mass of compound (10) and/or 0.00001 to 0.8 parts by mass of compound (11), more preferably 0.00001 to 0.5 parts by mass of compound (10) and/or 0.00001 to 0.5 parts by mass of compound (11), and particularly preferably 0.0001 to 0.1 parts by mass of compound (10) and/or 0.0001 to 0.1 parts by mass of compound (11), based on 100 parts by mass of compound (1).

Preferred specific examples of polar solvents include alcohol solvents, ether solvents, ester solvents, and nitrile solvents.

Preferred specific examples of alcohol solvents include methanol, ethanol, isopropanol, and tert-butyl alcohol.

Preferred specific examples of ester solvents include methyl formate, ethyl formate, methyl acetate, ethyl acetate, isopropyl acetate, methyl propionate, ethyl propionate, and n-butyl acetate.

Preferred specific examples of nitrile solvents include 1,4-dicyanobutane, acetonitrile, and benzonitrile.

Preferred specific examples of ether solvents include diethylene glycol dimethyl ether, triethylene glycol dimethyl ether, tetraethylene glycol dimethyl ether, diethyl ether, diisopropyl ether, dioxane, tetrahydrofuran, and 1,2-dimethoxyethane.

Preferred specific examples of polar solvents include methanol, ethanol, isopropanol, tert-butyl alcohol, diethylene glycol dimethyl ether, triethylene glycol dimethyl ether, tetraethylene glycol dimethyl ether, 1,4-dicyanobutane, acetonitrile, and tetrahydrofuran.

Preferred examples of polymerization inhibitors include 4-methoxy-1-naphthol, hydroquinone, hydroquinone methyl ether, dimethyl-t-butylphenol, 2,6-di-tert-butyl-p-cresol, and benzotriazole.

The quantitative ratio of compound (3) in the composition is preferably 0.00001 to 10 parts by mass, more preferably 0.00001 to 8 parts by mass, even more preferably 0.00001 to 5 parts by mass, and particularly preferably 0.0001 to 1 part by mass, based on 100 parts by mass of compound (1).

The quantitative ratio of compound (4-1) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (1).

The quantitative ratio of compound (4-2) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (1).

The quantitative ratio of the polar solvent in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (1).

The quantitative ratio of the polymerization inhibitor in the composition is preferably 0.00001 to 1 part by mass, more preferably 0.00001 to 0.8 parts by mass, even more preferably 0.00001 to 0.5 parts by mass, and particularly preferably 0.00001 to 0.1 parts by mass, based on 100 parts by mass of compound (1).

The quantitative ratio of water in the composition is preferably 0.00001 to 0.1 parts by mass, more preferably 0.00001 to 0.08 parts by mass, even more preferably 0.00001 to 0.05 parts by mass, and particularly preferably 0.00001 to 0.01 parts by mass, based on 100 parts by mass of compound (1).

Within the range of the above quantitative ratios, the composition of the present disclosure can be suitably used, for example, as a raw material for producing compound (5).

Although the embodiments are described above, it will be understood that various changes in form and details can be made without departing from the spirit and scope of the claims.

The present disclosure includes, for example, the following embodiments.

Item 1.

A method for producing a compound represented by formula (1)

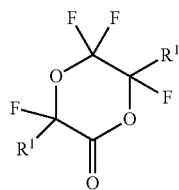

(1)

wherein two $R^1$ are the same and each is a fluorine atom or a fluoroalkyl group,
the method comprising step A of reacting a compound represented by formula (2):

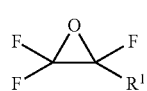

(2)

wherein $R^1$ is as defined above, with a compound represented by formula (3):

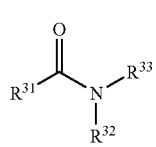

(3)

wherein $R^{31}$, $R^{32}$, and $R^{33}$ are the same or different and each is a hydrogen atom or an alkyl group, or two of them are optionally linked to each other to form a ring optionally having one or more substituents; and
at least one compound (4) selected from the group consisting of:
a compound represented by formula (4-1):

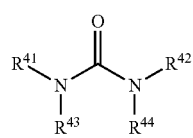

(4-1)

wherein $R^{41}$, $R^{42}$, $R^{43}$, and $R^{44}$ are the same or different and each is a hydrogen atom or an alkyl group, or two of them are optionally linked to each other to form a ring optionally having one or more substituents; and
a compound represented by formula (4-2):

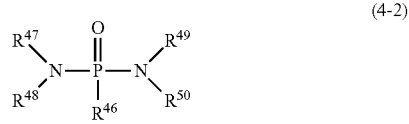

(4-2)

wherein $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{48}$ and $R^{50}$ are optionally linked to each other to form a ring optionally having one or more substituents, or $R^{49}$ and $R^{50}$ are optionally linked to each other to form a ring optionally having one or more substituents.

Item 2.

The production method according to Item 1, wherein step A is performed in the presence of an organic solvent, provided that the compounds represented by formulas (3) and (4) are excluded from the organic solvent.

Item 3.

The production method according to Item 1 or 2, wherein step A is a step of generating an upper liquid layer and a lower liquid layer, and the method further comprises step B of separating these layers.

Item 4.

The production method according to any one of Items 1 to 3, wherein compound (4) is a compound represented by formula (4-1).

Item 5.

The production method according to any one of Items 1 to 4, wherein $R^{41}$, $R^{42}$, $R^{43}$, and $R^{44}$ are the same or different and each is a hydrogen atom or a $C_{1-10}$ alkyl group, or two of them are optionally linked to each other to form a ring optionally having one or more substituents.

Item 6.

The production method according to any one of Items 1 to 5, wherein $R^{41}$ and $R^{42}$ are the same or different and each is a $C_{1-5}$ alkyl group, and $R^{43}$ and $R^{44}$ are the same or different and each is a $C_{1-5}$ alkyl group, or are linked to each other to form a ring optionally having one or more substituents.

Item 7.

The production method according to any one of Items 1 to 6, wherein the compound represented by formula (4-1) is at least one compound selected from the group consisting of N,N'-dimethylpropylene urea, N,N'-dimethylethylene urea, and tetramethyl urea.

Item 8.

The production method according to any one of Items 4 to 7, wherein in step A, the compound represented by formula (2) is supplied as gas, the amount of the compound represented by formula (2) is 70 mass % to 99.8 mass % based on the weight of the gas, and the amount of the compound represented by formula (4-1) is 0.001 to 0.3 mol per mol of the compound represented by formula (2).

Item 9.

The production method according to any one of Items 4 to 8, wherein step A does not include CsF.

Item 10.

The production method according to any one of Items 1 to 3, wherein compound (4) is a compound represented by formula (4-2).

Item 11.

The production method according to Items 1 to 3 or 10, wherein $R^{45}$ is a $C_{1-4}$ alkyl group, a 1-pyrrolidinyl group, a 1-piperidinyl group, a phenyl group optionally substituted with one, two, or three $C_{1-4}$ alkyl groups, or an amino group substituted with two $C_{1-4}$ alkyl groups, $R^{47}$, $R^{48}$, $R^{49}$, and $R^{50}$ are the same or different and each is a hydrogen atom or a $C_{1-4}$ alkyl group, or $R^{47}$ and $R^{48}$ are optionally linked to each other to form a pyrrolidine ring or a piperidine ring, $R^{48}$ and $R^{50}$ are optionally linked to each other to form a pyrrolidine ring or a piperidine ring, or $R^{49}$ and $R^{50}$ are optionally linked to each other to form a pyrrolidine ring or a piperidine ring.

Item 12.

The production method according to any one of Items 1 to 3, or 10 or 11, wherein the compound represented by formula (4-2) is hexamethylphosphoric triamide and/or tripyrrolidinophosphine oxide.

Item 13.

The production method according to any one of Items 10 to 12, wherein in step A, the compound represented by formula (2) is supplied as gas, the amount of the compound represented by formula (2) is 90 mass % to 99.8 mass % based on the weight of the gas, and the amount of the compound represented by formula (4-2) is 0.005 to 0.05 mol per mol of the compound represented by formula (2).

Item 14.

A method for producing a compound represented by formula (5):

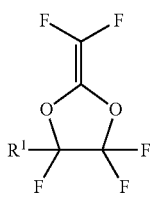

(5)

wherein $R^1$ is a fluorine atom or a fluoroalkyl group, the method comprising:

step C of heating a compound represented by formula (1) produced in step A or B:

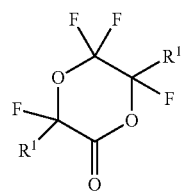

(1)

wherein two $R^1$ are the same and each is a fluorine atom or a fluoroalkyl group, in the presence of at least ore fluorine compound (9) selected from the group consisting of:

a compound represented by formula (9-1):

$MH_nF_m$ (9-1)

wherein M is a metal atom, n is 0 or 1, and the sum of the valence number of M and n is m;

a compound represented by formula (9-2):

$LR^{91}{}_4F$ (9-2)

wherein L is a nitrogen atom or a phosphorus atom, and $R^{91}$ are the same or different and each is a $C_{1-5}$ alkyl group; and hydrofluoric acid or a salt thereof, to produce a compound represented by formula (6):

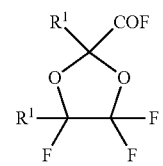

(6)

wherein $R^1$ are as defined above;

step D of reacting the compound represented by formula (6) with a base to produce a compound represented by formula (8):

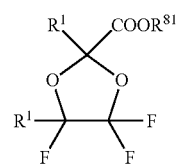

(8)

wherein $R^{81}$ is a group corresponding to the base, and $R^1$ are as defined above; and step E of heating the compound represented by formula (8) to produce the compound represented by formula (5).

Item 15.

The production method according to Item 14, comprising, in place of step D:

step D1 of reacting the compound represented by formula (6) with water or alkyl alcohol to produce a compound represented by formula (7):

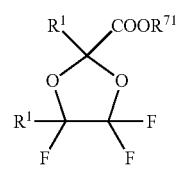

(7)

wherein $R^{71}$ is a hydrogen atom or an alkyl group, and $R^1$ are as defined above; and step D2 of reacting the compound represented by formula (7) with a base to produce the compound represented by formula (8).

Item 16.

The production method according to Item 15, further comprising step D1a of purifying a product of step D1 to obtain the compound represented by formula (7).

Item 17.

The production method according to Item 14, comprising, in place of steps D and E, step F of heating the compound represented by formula (6) in the presence of a base to produce the compound represented by formula (5).

Item 18.

A composition comprising a compound represented by formula (1):

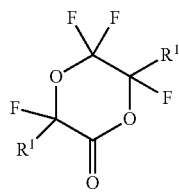
(1)

wherein two $R^1$ are the same and each is a fluorine atom or a fluoroalkyl group, and further comprising, based on 100 parts by mass of the compound represented by formula (1), 0.00001 to 1 part by mass of a compound represented by formula (10):

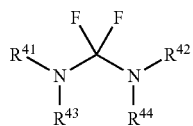
(10)

wherein $R^{41}$, $R^{42}$, $R^{43}$, and $R^{44}$ are the same or different and each is a hydrogen atom or an alkyl group, or two of them are optionally linked to each other to form a ring optionally having one or more substituents; and/or 0.00001 to 1 part by mass of a compound represented by formula (11):

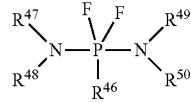
(11)

wherein $R^{46}$ is a hydrogen atom, an organic group, or an amino group optionally having one or more substituents, $R^{47}$, $R^{48}$, $R^{49}$, and $R^{50}$ are the same or different and each is a hydrogen atom or an alkyl group, or $R^{47}$ and $R^{48}$ are optionally linked to each other to form a ring optionally having one or more substituents, $R^{48}$ and $R^{50}$ are optionally linked to each other to form a ring optionally having one or more substituents, or $R^{49}$ and $R^{50}$ are optionally linked to each other to form a ring optionally having one or more substituents.

Item 19.

The composition according to Item 18, wherein the compound represented by formula (10) is contained in an amount of 0.00001 to 0.5 parts by mass, and/or the compound represented by formula (11) is contained in an amount of 0.00001 to 0.5 parts by mass, based on 100 parts by mass of the compound represented by formula (1).

EXAMPLES

An embodiment of the present disclosure is described in more detail below with Examples; however, the present disclosure is not limited thereto.

The symbols and abbreviations in the Examples are used with the following meanings.

DMF: N,N-dimethylformamide diglyme: diethylene glycol dimethyl ether

GC: gas chromatography

HMPA: hexamethylphosphoric triamide

CsF: cesium fluoride

Compound 1a: A Compound Represented by the Following Formula (1a):

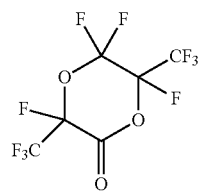
(1a)

Compound 6a: A Compound Represented by the Following Formula (6a):

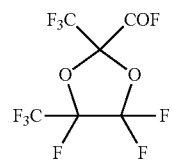
(6a)

Compound 8a: A Compound Represented by the Following Formula (8a):

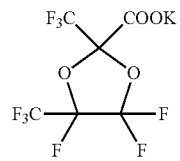
(8a)

Compound 5a: A Compound Represented by the Following Formula (5a):

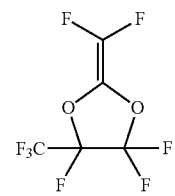
(5a)

Compound 8b: A Compound Represented by the Following Formula (8b):

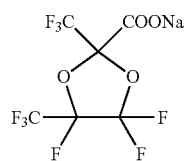

Compound 7a: A Compound Represented by the Following Formula (7a):

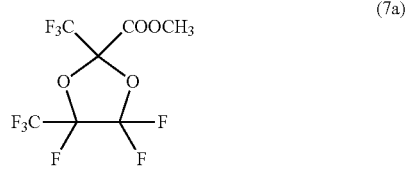 [SMILES: COC(=O)C1(C(F)(F)F)OC(F)(F)C(F)(C(F)(F)F)O1]

Compound 12: A Compound Represented by the Following Formula (12):

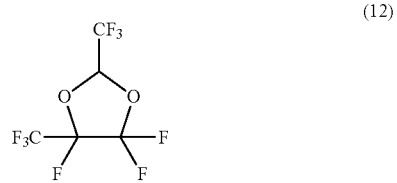 [SMILES: FC(F)(F)C1OC(F)(F)C(F)(C(F)(F)F)O1]

Example 1: Steps A and B 0.8 g of tetramethyl urea (7.0 mol), 5.1 g of DMF (70 mmol), and 9.4 g of diglyme (70 mmol) were added to a reactor and cooled to −20° C. 24 g of hexafluoropropylene oxide (0.14 mol) was added to the reactor at −20° C., and the mixture was stirred at room temperature for 1 hour. After the hexafluoropropylene oxide disappeared, the reaction liquid was collected. The reaction liquid is the composition of the present disclosure. The reaction liquid was separated in two layers: an upper layer liquid and a lower layer liquid. The reaction liquid was separated, and 19 g of the upper layer liquid and 20 g of the lower layer liquid were each collected. The lower layer liquid was analyzed by GC. Compound 1a at 73 GC % was obtained with a yield of 70%. Tetrafluoromethyl urea (compound (10)) in the lower layer was 0.1 GC %. The tetrafluoromethyl urea is a mixture of fluorides in which at least one hydrogen atom of the methyl group in tetramethyl urea is replaced by a fluorine atom.

Example 2: Steps A and B 0.3 g of HMPA (1.6 mmol), 5.7 g of DMF (78 mmol), and 10 g of diglyme (78 mmol) were added to a reactor and cooled to −20° C. 26 g of hexafluoropropylene oxide (0.15 mol) was added to the reactor at −20° C., and the mixture was stirred at room temperature for 1 hour. After the hexafluoropropylene oxide disappeared, the reaction liquid was collected. The reaction liquid was separated in two layers: an upper layer liquid and a lower layer liquid. The reaction liquid was separated, and 19 g of the upper layer liquid and 22 g of the lower layer liquid were each collected. The lower layer liquid was analyzed by GC. Compound 1a at 65 GC % was obtained with a yield of 54%. Compound (11) in the lower layer was 0.2 GC %.

Reference Example 1

0.83 g of CsF (2.5 mmol), 9.03 g of DMF (0.12 mol), and 16.6 g of diglyme (0.12 mol) were added to a reactor and cooled to −20° C. 44 g of hexafluoropropylene oxide (0.27 mol) was added to the reactor, and the mixture was stirred for 2 hours. After the hexafluoropropylene oxide disappeared, the reaction liquid was collected. The reaction liquid was separated in two layers: an upper layer liquid and a lower layer liquid. The reaction liquid was separated, and 29 g of the upper layer liquid and 40 g of the lower layer liquid were each collected. The lower layer liquid was analyzed by GC. Compound 1a at 63 GC % was obtained with a yield of 52%.

Comparative Example 1: Synthesis of Compound 1a in Two Steps 4.27 g of DMF (0.06 mol) was added to a reactor and cooled to −27° C. 12 g of hexafluoropropylene oxide (0.07 mol) was added to the reactor, and the mixture was stirred for 1 hour. After stirring, the reaction liquid was collected. The reaction liquid was analyzed by NMR. 4-Fluoro-5-oxo-2,4-bis(trifluoromethyl)-1,3-dioxolane-2-carbonyl fluoride, which was a precursor of the target product, was obtained with a yield of 5%. The yield was considered to be low because HCl gas was not used in this synthesis. Due to the very low yield of the precursor, the second step was not performed.

Example 3: Step C 13 g of a lower layer liquid (containing 9 g of compound 1a) obtained in the same manner as in Example 1, 2.3 g of CsF (15 mmol), and 4.0 g of diglyme (30 mmol) were added to a reactor, and heated at 120° C. for 12 hours to obtain a reaction liquid. In the reaction liquid, the upper layer liquid and the lower layer liquid were analyzed by GC. 12 g of compound 6a was obtained at a purity of 60%.

Example 4: Step D 9.8 g of a lower layer liquid containing compound 6a at a purity of 74% obtained in the same manner as in Example 3 was added to 3.2 g of potassium carbonate (0.02 mol) and 23 g of dimethoxyethane (0.26 mol), and the mixture was stirred at 60° C. for 2 hours to obtain a reaction liquid. The reaction liquid was filtered to obtain a filtrate, and the filtrate was concentrated. As a result of NM analysis, a concentrate containing 8.8 g of compound 8a was obtained (yield: 44%).

Example 5: Step E 6.7 g of compound 8a obtained in the same manner as in Example 4 was added to a reactor, and heated at 200° C. for 4 hours and at 300° C. for 1 hour. The resulting product was collected in a trap at −78° C. and analyzed by NM and GC. As a result, compound 5a was obtained with a yield of 60% and at a purity of 95%.

Example 6: Step E

Compound 8b was obtained in the same manner as in Example 4, except that the potassium carbonate was changed to 0.02 mol of sodium carbonate. 8.1 g of compound 8b and 24 g of triglyme were added to a reactor, and heated at 120° C. for 0.5 hours. The resulting product was collected in a trap at −78° C. and analyzed by NM and GC. As a result, compound 5a was obtained at a conversion of 65% and with a selectivity of 88%, and compound 12 was obtained with a selectivity of 12%.

Example 7: Step D1

3.2 g (0.1 mol) of methanol and 10 g of water were added to 22 g of the liquid obtained in Example 3, and the mixture was stirred for 2 hours. The product liquid was separated in two layers, and the lower layer liquid was collected by liquid separation, thereby obtaining compound 7a at a purity of 50% (GC). The yield was 58I.

Example 8: Step D2

0.09 mol of sodium hydroxide was added to 70 g of methanol in a glass reactor. 0.09 mol of compound 7a was gradually added to the methanol solution, and the mixture was stirred at 20° C. for 1 hour. The solvent was removed from the reaction liquid in a concentrator, and the resulting solid was collected. This solid was dried under reduced pressure to obtain a stoichiometric amount of compound 8b.

The invention claimed is:

1. A method for producing a compound represented by formula (1):

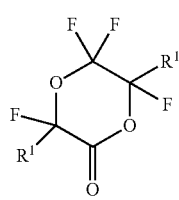

(1)

wherein two $R^1$ are the same and each is a fluorine atom or a fluoroalkyl group,
the method comprising step A of reacting a compound represented by formula (2):

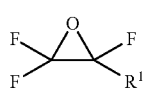

(2)

wherein $R^1$ is as defined above, with a compound represented by formula (3):

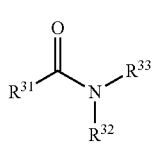

(3)

wherein $R^{31}$, $R^{32}$, and $R^{33}$ are the same or different and each is a hydrogen atom or an alkyl group, or two of them are optionally linked to each other to form a ring optionally having one or more substituents; and
a compound represented by formula (4-1):

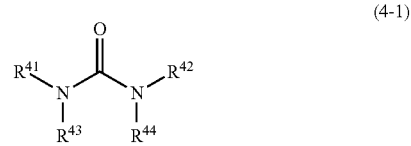

(4-1)

wherein $R^{41}$, $R^{42}$, $R^{43}$, and $R^{44}$ are the same or different and each is a hydrogen atom or an alkyl group, or two of them are optionally linked to each other to form a ring optionally having one or more substituents.

2. The production method according to claim 1, wherein step A is performed in the presence of an organic solvent, provided that the compounds represented by formulas (3) and (4-1) are excluded from the organic solvent.

3. The production method according to claim 1, wherein step A is a step of generating an upper liquid layer and a lower liquid layer, and the method further comprises step B of separating these layers.

4. The production method according to claim 1, wherein $R^{41}$, $R^{42}$, $R^{43}$, and $R^{44}$ are the same or different and each is a hydrogen atom or a $C_{1-10}$ alkyl group, or two of them are optionally linked to each other to form a ring optionally having one or more substituents.

5. The production method according to claim 1, wherein $R^{41}$ and $R^{42}$ are the same or different and each is a $C_{1-5}$ alkyl group, and $R^{43}$ and $R^{44}$ are the same or different and each is a $C_{1-5}$ alkyl group, or are linked to each other to form a ring optionally having one or more substituents.

6. The production method according to claim 1, wherein the compound represented by formula (4-1) is at least one compound selected from the group consisting of N,N'-dimethylpropylene urea, N,N'-dimethylethylene urea, and tetramethyl urea.

7. The production method according to claim 1, wherein in step A, the compound represented by formula (2) is supplied as gas, the amount of the compound represented by formula (2) is 70 mass % to 99.8 mass % based on the weight of the gas, and the amount of the compound represented by formula (4-1) is 0.001 to 0.3 mol per mol of the compound represented by formula (2).

8. The production method according to claim 1, wherein step A does not include CsF.

9. A method for producing a compound represented by formula (5):

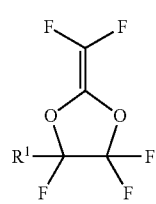

(5)

wherein $R^1$ is a fluorine atom or a fluoroalkyl group, the method comprising:

step of producing a compound represented by formula (1) by step A according to claim 1, optionally wherein step A is a step of generating an upper liquid layer and a lower liquid layer, and the method further comprises separating these layers:

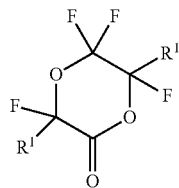

(1)

wherein two $R^1$ are the same and each is a fluorine atom or a fluoroalkyl group; and steps C of heating the compound represented by formula (1) produced in above step in the presence of at least one fluorine compound (9) selected from the group consisting of:

a compound represented by formula (9-1):

$$MH_nF_m \qquad (9\text{-}1)$$

wherein M is a metal atom, n is 0 or 1, and the sum of the valence number of M and n is m;

a compound represented by formula (9-2):

$$LR^{91}{}_4F \qquad (9\text{-}2)$$

wherein L is a nitrogen atom or a phosphorus atom, and $R^{91}$ are the same or different and each is a $C_{1\text{-}5}$ alkyl group; and hydrofluoric acid or a salt thereof, to produce a compound represented by formula (6):

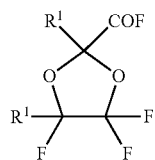

(6)

wherein $R^1$ are as defined above;

step D of reacting the compound represented by formula (6) with a base to produce a compound represented by formula (8):

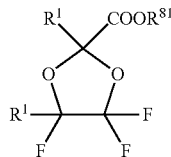

(8)

wherein $R^{71}$ is a group corresponding to the base, and $R^1$ are as defined above; and step E of heating the compound represented by formula (8) to produce the compound represented by formula (5).

10. The production method according to claim 9, comprising, in place of step D:

step D1 of reacting the compound represented by formula (6) with water or alkyl alcohol to produce a compound represented by formula (7):

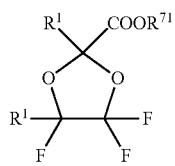

(7)

wherein $R^{71}$ is a hydrogen atom or an alkyl group, and $R^1$ are as defined above; and step D2 of reacting the compound represented by formula (7) with a base to produce the compound represented by formula (8).

11. The production method according to claim 10, further comprising step D1a of purifying a product of step D1 to obtain the compound represented by formula (7).

12. The production method according to claim 9, comprising, in place of steps D and E, step F of heating the compound represented by formula (6) in the presence of a base to produce the compound represented by formula (5).

* * * * *